(12) United States Patent
Sagerer-Gerhardt et al.

(10) Patent No.: US 12,150,706 B2
(45) Date of Patent: Nov. 26, 2024

(54) HEART CATHETER FOR ENDOCARDIAL LASER IRRADIATION AND LASER SYSTEM

(71) Applicant: LASCOR GMBH, Taufkirchen (DE)

(72) Inventors: Michaela Sagerer-Gerhardt, Taufkirchen (DE); Helmut Weber, Taufkirchen (DE)

(73) Assignee: LASCOR GMBH, Taufkirchen (DE)

( * ) Notice: Subject to any disclaimer, the term of this patent is extended or adjusted under 35 U.S.C. 154(b) by 862 days.

(21) Appl. No.: 17/294,666

(22) PCT Filed: Nov. 19, 2019

(86) PCT No.: PCT/EP2019/081712
§ 371 (c)(1),
(2) Date: May 17, 2021

(87) PCT Pub. No.: WO2020/104407
PCT Pub. Date: May 28, 2020

(65) Prior Publication Data
US 2021/0401498 A1    Dec. 30, 2021

(30) Foreign Application Priority Data
Nov. 19, 2018   (EP) .................................... 18206951

(51) Int. Cl.
*A61B 18/24*   (2006.01)
*A61B 18/00*   (2006.01)

(52) U.S. Cl.
CPC .... *A61B 18/24* (2013.01); *A61B 2018/00178* (2013.01); *A61B 2018/00357* (2013.01);
(Continued)

(58) Field of Classification Search
CPC .......... A61B 18/24; A61B 2018/00178; A61B 2018/00357; A61B 2018/00577; A61B 2218/002
USPC ......................................................... 606/15
See application file for complete search history.

(56) References Cited

U.S. PATENT DOCUMENTS

2002/0042639 A1\*   4/2002   Murphy-Chutorian ...................... A61B 18/24 607/89
2003/0060867 A1\*   3/2003   Weber .................... A61B 18/24 607/122

(Continued)

FOREIGN PATENT DOCUMENTS

DE    3814847 A1     11/1989
EP    1290981 A2     3/2003
EP    3095404 A1 \*  11/2016  .......... A61B 18/1492

OTHER PUBLICATIONS

European Patent Office, Extended European Search Report Issued in Application No. 18206951.8, Mar. 25, 2019, Germany, 8 pages.

(Continued)

*Primary Examiner* — Aaron F Roane
(74) *Attorney, Agent, or Firm* — McCoy Russell LLP

(57) ABSTRACT

A heart catheter for endocardial laser irradiation of arrhythmogenic substrates is disclosed. The heart catheter comprises a catheter hose enclosing a flushing channel and an optical fiber, and a distal catheter tip. The catheter tip comprises: a main body surrounding a frontal passageway for laser light emitted from the optical fiber and for a flushing liquid provided via the flushing channel; a fiber mount inwardly extending from the main body, for centrally mounting the optical fiber; and connecting channels segmenting the fiber mount in a circumferential direction and connecting the flushing channel with the frontal passageway. Since the frontal passageway narrows, at least within a (Continued)

longitudinal section thereof, towards the distal end of the catheter tip, the flushing liquid can flow in an even and laminar manner through the passageway, thereby keeping blood out of the irradiation field and away from the optical fiber.

14 Claims, 3 Drawing Sheets

(52) U.S. Cl.
CPC ............... *A61B 2018/00577* (2013.01); *A61B 2218/002* (2013.01)

(56) References Cited

U.S. PATENT DOCUMENTS

| | | | |
|---|---|---|---|
| 2011/0270244 A1* | 11/2011 | Clark | A61B 18/1492 606/41 |
| 2013/0310825 A1 | 11/2013 | Pappone et al. | |
| 2014/0133814 A1* | 5/2014 | Stevens | A61B 18/24 385/117 |
| 2016/0183821 A1 | 6/2016 | Pai et al. | |

OTHER PUBLICATIONS

ISA European Patent Office, International Search Report Issued in Application No. PCT/EP2019/081712, Dec. 18, 2019, WIPO, 3 pages.

* cited by examiner

HEART CATHETER FOR ENDOCARDIAL LASER IRRADIATION AND LASER SYSTEM

CROSS REFERENCE TO RELATED APPLICATIONS

The present application is a U.S. National Phase of International Application No. PCT/EP2019/081712 entitled "HEART CATHETER FOR ENDOCARDIAL LASER IRRADIATION AND LASER SYSTEM," and filed on Nov. 19, 2019. International Application No. PCT/EP2019/081712 claims priority to European Patent Application No. 18206951.8 filed on Nov. 19, 2018. The entire contents of each of the above-listed applications are hereby incorporated by reference for all purposes.

TECHNICAL FIELD

The present invention relates to a heart catheter for endocardial laser irradiation according to the preamble of claim 1, as published in EP 1 290 981 A1, and a laser system.

BACKGROUND AND SUMMARY

Catheter ablation of arrhythmogenic cardiac substrates is a technique for the treatment of various arrhythmias of the heart, based on heating or cooling particular portions of the cardiac walls in an effort to abolish abnormal focal or diffuse electrical activity or to block abnormal electrical conduction permanently. The myocardial scars thereby produced should be limited to the culprit tissue, without damage to the adjacent healthy myocardium, without jeopardizing the pumping function of the heart. The diseased myocardium is rendered electrically inactive; the patient is cured from the arrhythmia.

A promising catheter ablation technique is based on the use of infrared laser light for inducing transmural lesions of coagulation necrosis without heating of the catheter itself. This technique is based on transmitting highly divergent laser light through a corridor of clear flushing liquid keeping blood out of the irradiation field and cooling the irradiated substrate during laser irradiation. Thus, overheating of the irradiated cardiac substrate can be avoided, as well as dissipation of light energy into blood and damage of the optical fiber due to contamination with blood.

This technique can be performed with the catheter published in EP 1 290 981 A1, taking advantage of the selective absorption of laser light in the various cardiac structures and of an improved control of the growing lesions by deflection of intracardiac potentials from the irradiation site. To this end, the catheter comprises a rigid distal tip with outer electrodes, enclosing a frontal passageway with a distal opening for the laser light and flushing liquid. The catheter is positioned on target areas by means of pre-shaped and/or steerable guiding catheters or robotic systems known per se.

During laser irradiation in the beating heart, however, it can be difficult to maintain an ideal orthogonal position of the catheter tip on the targeted area. This deteriorates the shielding of the frontal passageway from the surrounding blood. Thus, laser irradiation of the targeted substrates may become ineffective due to dissipation of light energy, and/or blood constituents may adhere to the optical fiber. The latter instance may require replacement of the laser catheter. It is an object of the present invention to address the above drawbacks of the currently used laser catheter system.

The posed object is achieved with a heart catheter according to claim 1. The heart catheter is configured for endocardial laser irradiation of arrhythmogenic substrates, and comprises a catheter hose enclosing a flushing channel and an optical fiber.

The heart catheter further comprises a distal catheter tip with:
- a main body surrounding a frontal passageway for laser light emitted from the optical fiber, and for a flushing liquid provided via the flushing channel;
- a fiber mount inwardly extending from the main body, for centrally mounting the optical fiber; and
- connecting channels segmenting the fiber mount in a circumferential direction and connecting the flushing channel with the frontal passageway.

According to the invention, the frontal passageway narrows, at least within a longitudinal section thereof, towards the distal end of the catheter tip. For example, the frontal passageway can narrow within a distal section thereof and/or a middle section thereof and/or a proximal section thereof.

Contrary to the emitted laser light that widens towards the distal end of the catheter tip, the efficacy of flushing surprisingly improves if the frontal passageway narrows in the distal direction. This advantage is mainly achieved by slightly focusing the flow of the flushing liquid, thereby reducing turbulent flow components and eventually resulting in an even and more powerful flow of the flushing liquid. Thus, blood can be kept out of the irradiation field and away from the optical fiber. Moreover, it is possible to suppress blood swirls at the distal border of the frontal passageway. Thus, damage of the optical fiber can be prevented and the efficacy of laser ablation of arrhythmogenic substrates can be improved.

A first distance between the distal end of the narrowing longitudinal section and the distal end of the catheter tip may be less than, or equal to 0.5 mm, in particular less than, or equal to 0.2 mm. Thus, the flow of the flushing liquid in the distal part of the frontal passageway, close to the targeted cardiac substrate, can be optimized.

A second distance between the proximal end of the narrowing longitudinal section and the distal end of the connecting channels may be less than, or equal to 1 mm, in particular less than, or equal to 0.5 mm. Thus, the flow of the flushing liquid in the proximal part of the frontal passageway can be optimized, in particular with regard to the position and shape of the connecting channels.

The passageway may narrow at an angle of 1 to 10° with regard to a central longitudinal axis of the frontal passageway. This is helpful to provide a laminar flow of the flushing liquid along the inner wall of the distal main body. Moreover, at least one longitudinal section of the passageway may narrow in a linear fashion. Nevertheless, at least one longitudinal section of the inner wall of the distal main body may comprise a convex and/or concave contour.

The cross-sectional area of the frontal passageway at the narrowest part thereof may be greater than the total cross-sectional area of the connecting channels at the distal end thereof by a factor of 1.5 to 3. This provides similar flow velocities in the connecting channels and in the frontal passageway, thereby contributing to an even and powerful flow of the flushing liquid.

The fiber mount may comprise ridges separately extending from the main body of the catheter tip to the optical fiber. The ridges may comprise free inner ends that do not touch each other. Preferably, the ridges extend from the distal main body in radial directions.

Thus, the cross-sectional area of the connecting channels can be maximized, thereby avoiding jet formation in the connecting channels. This is helpful to provide even laminar flow of the flushing liquid in the frontal passageway.

The fiber mount may comprise three evenly spaced ridges. Preferably, each of the ridges has a width of 0.2 to 0.3 mm at the inner ends thereof. This optimizes the cross-sectional area of the connecting channels and provides a stable fiber mount in an embodiment comprising three outer electrodes for the deflection of intracardiac potentials.

The ridges may comprise concave inner centering surfaces adapted to a cylindrical outer surface of the optical fiber. This provides particularly precise centering of the optical fiber and stable fixation by means of a glue such as a UV-curing acrylic, or an instant glue such as "Loctite 4031".

The ridges may comprise proximal sections extending from the main body of the catheter tip in a proximal direction and, in particular, being configured to radially support the flexible catheter hose. This is helpful to provide a stable and slightly flexible connection of the distal main body and the catheter hose. At the same time, the cross-sectional area for the flow of flushing liquid is maximized.

The proximal sections of the ridges may comprise longitudinal notches configured to support electric cables enclosed by the catheter hose (or leads running in the wall of the catheter hose). This simplifies the assembly of the heart catheter and provides a stable and reliable fixation of the cables (leads) at the main body of the catheter tip.

The heart catheter may further comprise electrodes extending from, or being connected with, electric cables enclosed by the catheter hose, the electrodes being supported by notches formed in an outer surface of the distal main body. The notches simplify the assembly of the heart catheter and provide stable and reliable fixation of the cable electrodes.

The cross-section of the notches may have a base formed as a segment of a circle, in particular extending over more than 180°, for instance over a segment of 190-270°. This enables exact guiding and/or positive locking of the electrodes, thereby simplifying the assembly of the heart catheter. Nevertheless, the electrodes can be fixed in the notches by means of a glue.

The electrodes may be stripped distal sections of the electric cables, in particular the distal sections being plated with gold, platinum or the like. This feature simplifies the assembly by avoiding soldering or welding of the electrodes and optimizes the stability of the electrode fixation.

The distal main body and the fiber mount may consist of an additively layered biocompatible plastic material, such as a material from the "Luxaprint" family, or other biocompatible plastic materials. Thus, the shapes of fiber mount, connecting channels and frontal passageway can be optimized in a flexible manner. The material of the distal main body and the fiber mount, in particular the additively layered material, has a higher rigidity (such as Shore D) than the material of the flexible catheter hose.

The optical fiber may be configured to emit the laser light at a full divergence angle of 40-80°. This feature avoids overheating of the cardiac substrate, in combination with the optimized flow of flushing liquid in the frontal passageway. The cardiac substrate may be irradiated with a laser power of 10-25 W.

Another variant of the heart catheter for endocardial laser irradiation of arrhythmogenic substrates can comprise a catheter hose enclosing a flushing channel and an optical fiber, and a distal catheter tip with:

a main body surrounding a frontal passageway for laser light emitted from the optical fiber and for a flushing liquid provided via the flushing channel;

a fiber mount inwardly extending from the main body, for centrally mounting the optical fiber; and connecting channels segmenting the fiber mount in a circumferential direction and connecting the flushing channel with the frontal passageway.

In this advantageous variant, the fiber mount comprises ridges separately extending from the distal main body to the optical fiber, wherein the ridges comprise free inner ends that do not touch each other.

Preferably, the ridges extend from the distal main body in radial directions.

This advantageous variant of the heart catheter provides an improved cross-section of the connecting channels, thereby avoiding jet formation in the connecting channels and turbulent flow of the flushing liquid in the adjoining frontal passageway. Thus, a uniform and strong flow of the flushing liquid can be provided in the frontal passageway, even in the case where the frontal passageway does not narrow in the distal direction.

Each of the described/claimed embodiments could also be based on this variant of the heart catheter. For instance, embodiments of this variant could differ from the described/claimed embodiments only in that features directed to the narrowing of the passageway are optional and the feature directed to ridges having free inner ends (not touching each other) is mandatory.

The posed object is further solved with a laser system for endocardial laser irradiation of arrhythmogenic substrates, wherein the laser system comprises: the heart catheter according to at least one of the embodiments described herein; a laser configured to be coupled with the heart catheter and to emit infrared (IR) laser light, in particular within a wavelength range of 950-1100 nm at a distal power of 10-25 W; and a flushing pump configured to be coupled with the heart catheter and to provide flushing liquid, in particular at a flow rate of 5-30 ml/min. This system improves the safety and efficacy of intracardiac laser ablation of arrhythmias.

BRIEF DESCRIPTION OF THE FIGURES

The invention will be described in more detail below with reference to preferred embodiments represented in the figures. In the drawings.

DETAILED DESCRIPTION

Figure 1:
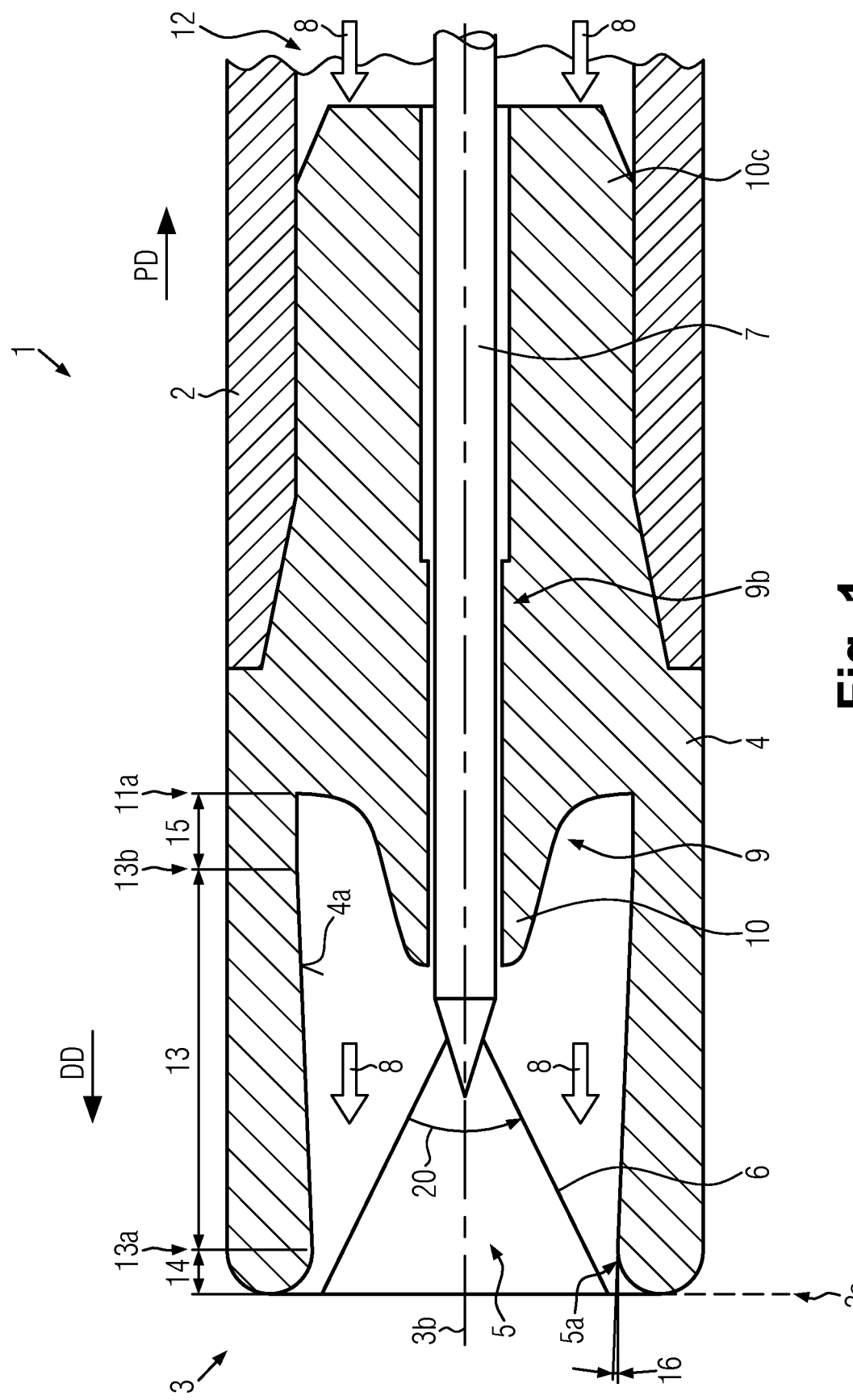
FIG. 1 shows a schematic longitudinal section through a distal portion of the laser catheter.

According to FIG. 1, the laser catheter 1 comprises an essentially flexible catheter hose 2 and an essentially rigid catheter tip 3 attached to the distal end of the catheter hose 2. The catheter tip 3 comprises a distal main body 4 with an inner wall 4a surrounding a frontal passageway 5 configured for the transmission of laser light 6 emitted from an optical fiber 7 and for the flushing of the distal catheter tip 3 with a flushing liquid 8 such as physiological saline solution. The flushing liquid 8 provides a clear optical corridor from the optical fiber 7 to the distal end of the frontal passageway 5 (formed by a circular opening at the distal end 3a of the catheter tip 3).

Figure 2:
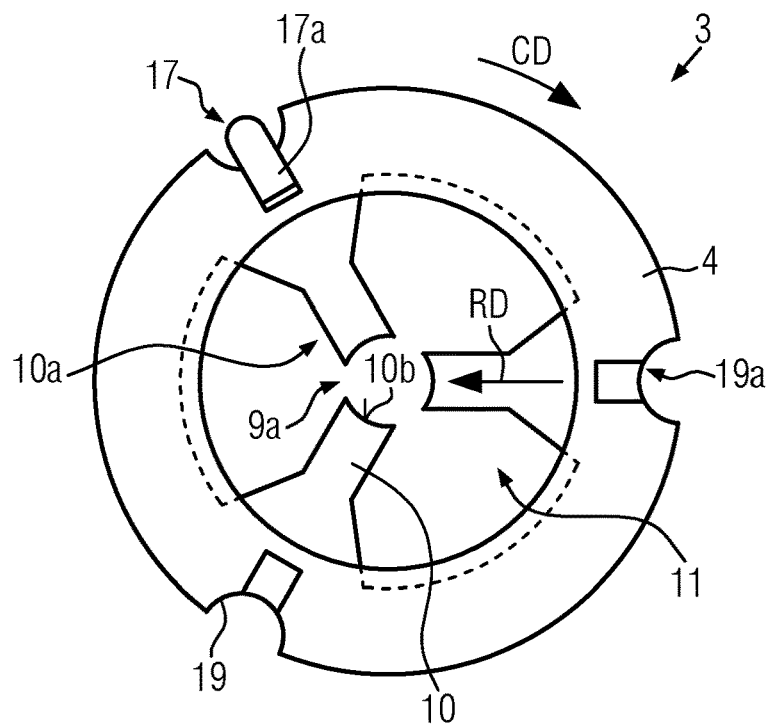
FIG. 2 shows a frontal view into the main body of the catheter tip.

The optical fiber 7 is positioned concentrically with regard to the frontal passageway 5 by means of a segmented fiber mount 9. As can be seen in FIG. 2, the fiber mount 9 comprises ridges 10 that inwardly extend from the main body 4 of the catheter tip 3. Preferably, the ridges 10 are evenly spaced from each other in a circumferential direction CD. Preferably, the ridges 10 are oriented in radial directions RD.

For the sake of simplicity, FIG. 1 shows a fiber mount 9 with two diametrically opposed ridges 10. FIG. 2 shows a preferable embodiment of the catheter tip 3 comprising three ridges 10. Nevertheless, the number of ridges 10 could deviate from the depicted embodiments.

Preferably, the free ends 10a of the ridges comprise concave inner mounting surfaces 10b adapted to the essentially cylindrical jacket of the optical fiber 7.

Preferably, the free ends 10a do not touch each other so that the fiber mount 9 comprises gaps 9a arranged (in the circumferential direction CD) between the free ends 10a of the ridges 10. The optical fiber 7 is preferably fixed in a proximal part 9b (FIG. 1) of the fiber mount 9 by means of a glue such as an UV-curing acrylic glue or instant acrylic glue (not shown).

The fiber mount 9 is segmented in the circumferential direction CD by connecting channels 11 connecting the frontal passageway 5 with a proximal flushing channel 12 (FIG. 1) provided in the catheter hose 2.

Preferably, the cross-sectional area of the frontal passageway 5 at its narrowest part 5a (FIG. 1) is by a factor of 1.5 to 3 greater than the total cross-sectional area of the connecting channels 11 at the distal ends 11a thereof, in an effort to establish a powerful and laminar flow of the flushing liquid 8. In FIG. 2, the corresponding hidden outer contours of the connecting channels 11 are drawn in broken lines.

The frontal passageway 5 comprises at least one longitudinal section 13 narrowing in a distal direction DD, towards the distal end 3a of the catheter tip 3. In an exemplary manner, FIG. 1 shows a first distance 14 provided between the distal end 13a of the narrowing longitudinal section 13 and the distal end 3a of the catheter tip 3. Preferably, the first distance 14 is no more than 0.5 mm, in particular no more than 0.2 mm. This optimizes the flushing near the distal border of the frontal passageway 5.

In an exemplary manner, FIG. 1 further shows a second distance 15 provided between the proximal end 13b of the narrowing longitudinal section 13 and the distal end 11a of the connecting channels 11. Preferably, the second distance 15 is no more than 1 mm, in particular no more than 0.5 mm. This can establish an even and essentially laminar flow of the flushing liquid 8 in the region of the fiber mount 9.

However, the first distance 14 and/or the second distance 15 is/are merely optional. In other words, the narrowing longitudinal section 13 could extend to the distal end 3a of the catheter tip 3 and/or directly adjoin the connecting channels 11. Thus, the frontal passageway 5 could narrow over its whole length, from the distal end 11a to the distal end 3a, as well.

In an exemplary manner, FIG. 1 shows that the frontal passageway 5 narrows at an angle 16 of preferably 1 to 10° with regard to the central longitudinal axis 3b of the catheter tip 3. The frontal passageway 5 can taper in a linear fashion. However, convex and/or concave longitudinal contours of the frontal passageway 5 (of the inner wall 4a) are possible as well.

Figure 3:
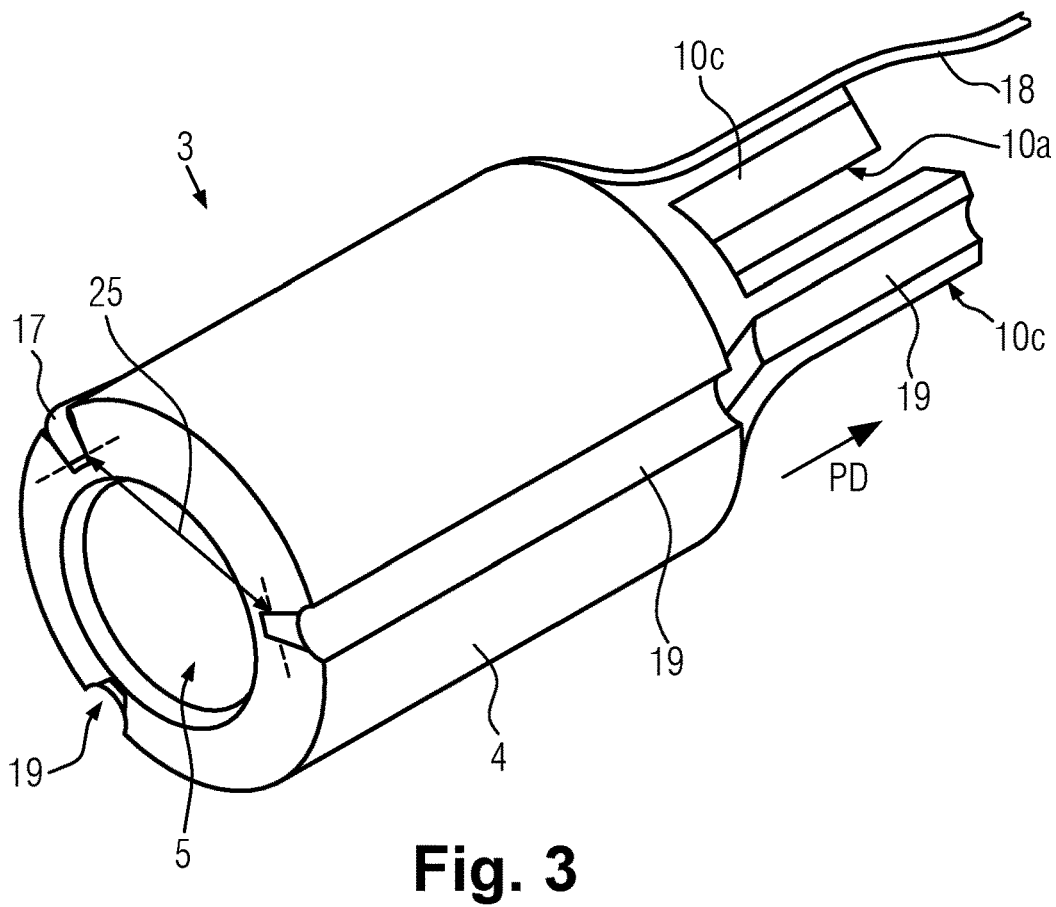
FIG. 3 shows an oblique view of the main body and the proximal sections of the ridges.

FIGS. 2 and 3 show that the catheter tip 3 further comprises outer electrodes 17 configured to deflect electrical potentials from the targeted cardiac substrate. The electrodes 17 can be formed by stripping and plating the distal ends of cables 18 running inside the proximal flushing channel 12 of the catheter hose 2.

In FIGS. 2 and 3, only one out of three electrodes 17 is shown with its distal end 17a bent towards the frontal passageway 5. The electrodes 17 are mounted in longitudinal notches 19 formed in the outer surface of the main body 4 of the catheter tip 3.

As can be seen from FIGS. 1 and 3, the ridges 10 comprise proximal sections 10c extending from the main body 4 in a proximal direction PD. The proximal ridge sections 10c are configured for a radial support of the flexible catheter hose 2. The longitudinal notches 19 preferably extend along the proximal ridge sections 10c in order to support the electric cables 18 and/or the electrodes 17. In an effort to establish an even and powerful flow of the flushing liquid 8, the free ends 10a of the ridges 10 are separated from each other in the proximal sections 10c, as well.

The cross-sectional profile of the notches 19 can have a base 19a formed as a segment of a circle, in particular extending over an angle of more than 180° and preferably of 190-270°. This could enable positive locking of the electrodes 17, thereby simplifying the assembly of the heart catheter 1 and/or strengthening the fixation of the electrodes 17 in the notches 19. Nevertheless, the electrodes 17 are preferably fixed in the notches 19 in a well-known manner by means of a glue such as a biocompatible acrylic glue.

During therapeutic laser irradiation, which can be performed at a distal laser power of 10-25 W or the like, the flushing liquid 8 can be provided at a flow rate of 5-30 ml/min or the like. Under these circumstances, the geometry of the frontal passageway 5 provides an even and essentially laminar flow of the flushing liquid 8, thereby keeping blood out of the frontal passageway 5 including the beam path of the emitted laser light 6.

The laser light 6 is preferably emitted at a full divergence angle 20 of 60-80° in order to reduce the risk or superficial overheating at the irradiated cardiac substrate. To this end, the frontal passageway 5 (the inner wall 4a of the main body 4) is configured such that the laser light 6 can be provided with a beam diameter of preferably 1.3 to 1.8 mm at the distal end 3a of the catheter tip 3. According to the present invention, overheating is also effectively suppressed by the focused flow of the flushing liquid 8 towards the irradiated cardiac substrate.

Figure 4:
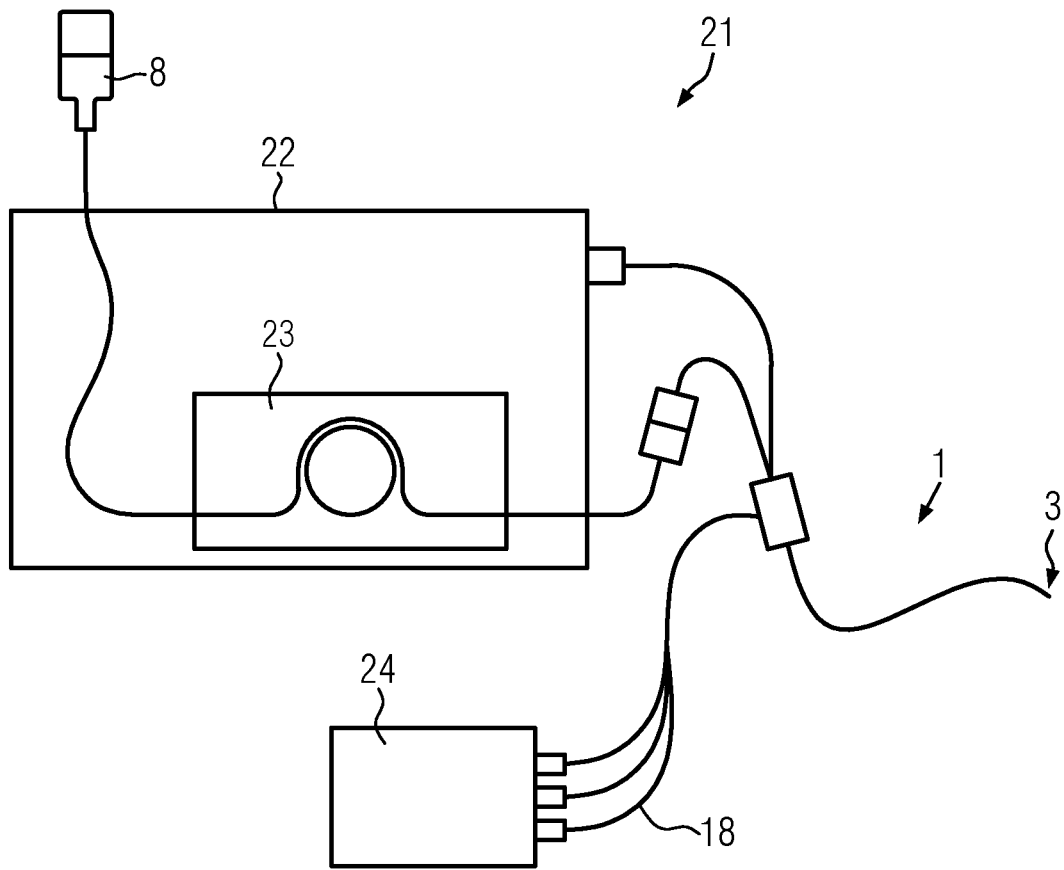
FIG. 4 shows a schematic view of a laser system.

FIG. 4 shows a laser system 21 comprising the heart catheter 1 and a laser 22 emitting in the IR wavelength range, preferably at a wavelength between 950 nm and 1100 nm. The heart catheter 1 can be optically coupled to the laser 22 by focusing optics and connectors known per se.

The laser system 21 further comprises a pump 23 such as a peristaltic pump for pumping sterile flushing liquid 8, in particular physiological saline solution, at a preset flow rate through the heart catheter 1 via its proximal flushing channel 12, the connecting channels 11 and the frontal passageway 5 to the targeted cardiac substrate. Preferably, the flow rate of the flushing liquid automatically increases with the onset of therapeutic laser irradiation. To this end, the pump 23 can be controlled by a footswitch of the laser 22 in a principally known manner. The electric cables 18 can be connected to an electrophysiological monitoring unit 24 as known per se.

The distal main body 4 of the catheter tip 3, including the fiber mount 8 with the ridges 10, preferably consists of an additively layered biocompatible plastic material such as a material from the "Luxaprint" family of materials.

The catheter hose 2 can be made from a standard catheter material such as Pebax 6333 SA01 compound with 20% $BaSO_4$.

The electrodes 17 can be formed by distally stripping the leads of the electric cables 18 and plating the stripped leads with gold, platinum or the like.

The core and the cladding of the optical fiber 7 can be made from fused silica, and the jacket can consist of polyimide. In order to produce highly divergent laser light 6, the distal end of the optical fiber 7 can be ground to a conical shape (exemplary shown in FIG. 1) as known per se.

It is to be understood that the connection between the optical fiber 7 and the fiber mount 9 is permanent in order to hold the optical fiber in an axially and radially fixed position with respect to the frontal passageway 5 and the distal end 3a of the catheter tip 3. This is important for an optimized laser irradiation of tissue located at the distal end 3a, in particular when compared with a temporary replacement of a guide wire in a cardiovascular sheath or the like by advancing an optical fiber to the distal end portion thereof.

The inner wall 4a preferably has a circular cross-section, as shown in FIGS. 1 to 3. However, in particular within the narrowing longitudinal section 13, the type of cross-section of the frontal passageway 5 may deviate from a rotationally symmetric configuration. Possible alternative or additional configurations include at least one of the following features: a polygonal cross-section; a rounded polygonal cross-section; ridges running on the inner wall 4a towards the distal end 3a; and notches running in the inner wall 4a towards the distal end 3a. Such ridges/notches could run along radial planes or take a helical course. Ridges/notches may be helpful to establish a more laminar flow in regions close to the distal end 3a. The type of inner cross-section could also change in the axial direction.

It is to be understood that the narrowing of the frontal passageway 5 is equivalent to gradually reducing the cross-sectional area thereof, regardless of the type of cross-section involved. Such a gradual reduction of the cross-sectional area focuses/strengthens laminar flow components, thereby suppressing undesirable turbulent flow components between the optical fiber 7 and the distal end 3a. This is particularly helpful to avoid undesirable transport of surrounding blood from the distal end 3a towards the optical fiber 7 by means of turbulent flow components.

In a preferred embodiment, the cross-sectional area of the frontal passageway at the narrowest part thereof may be greater than, or equal to, the total cross-sectional area of the connecting channels at the distal end thereof by a factor of 1 to 1.2.

In a preferred embodiment, the cross-sectional area of the frontal passageway at the narrowest part thereof may be smaller than, or equal to, the total cross-sectional area of the connecting channels at the distal end thereof. In particular, the ratio of the cross-sectional area of the narrowest part of the frontal passageway to the cross-sectional area of the connecting channels is 0.6 to 1, preferably 0.7 to 0.9. This provides optimized flow velocities in the connecting channels and in the frontal passageway, thereby providing a substantially laminar flow of the flushing liquid and reducing turbulent flow components in the frontal passageway. This keeps blood away from the light-emitting surface of the optical fiber.

For an optimal deflection of local electrical potentials from the targeted cardiac substrate, a cross-sectional clearance 25 (FIG. 2) of 1.60 mm to 2.00 mm, in particular 1.70 mm to 1.90 mm, is provided between the outer electrodes 17. This arrangement reduces additional deflection of far-field potentials that, otherwise, could disturb the deflection of the local potentials from the target site in an unwanted manner.

A cross-sectional circumcircle (not shown) around the outer electrodes 17 has a preferred diameter of 2.30 mm to 2.50 mm, in particular 2.35 mm to 2.45 mm.

To this end, three outer electrodes 17 can be provided on the catheter tip 3, the electrodes 17 resembling the corners of an equilateral triangle surrounding the distal cross-section of the frontal passageway 5. This provides three bipolar deflections between evenly spaced outer electrodes 17 for monitoring the ongoing electrical deactivation of the irradiated cardiac substrate.

In another preferred embodiment, the width (inner diameter) of the frontal passageway 5 (the inner wall 4a of the main body 4) is configured such that the laser light 6 can exit through the distal end 3a of the catheter tip with an outer beam diameter of 1.3 to 1.6 mm at the distal end 3.

Although the heart catheter according to at least one of the disclosed embodiments is configured for endocardial laser irradiation of arrhythmogenic substrates, it is also a catheter suitable for laser irradiation of other cardiovascular tissues, such as pulmonary veins, or for laser irradiation of renal vessels.

It is to be understood that the disclosed heart catheter is advanced to the target substrate inside an appropriate guiding catheter. Such guiding catheters are generally introduced in, and advanced through, vessels my means of sheaths and atraumatic dilators with tapered distal ends over guidewires as known per se. Before eventually advancing the disclosed heart catheter through the introduced guide catheter, the respective guidewire and dilator have to be removed therefrom.

Such a procedure provides fundamental improvements, in particular regarding safety issues, over procedures based on positioning a dilator/sheath at a vascular target site and temporarily replacing the guide wire inside the positioned dilator with an optical fiber for subsequent laser irradiation of the target site.

The invention claimed is:

1. A heart catheter for endocardial laser irradiation, with a catheter hose enclosing a flushing channel and an optical fiber, and with a distal catheter tip comprising:
   a main body surrounding a frontal passageway for laser light emitted from the optical fiber and for a flushing liquid provided via the flushing channel;
   a fiber mount inwardly extending from the main body, for centrally mounting the optical fiber; and
   connecting channels segmenting the fiber mount in a circumferential direction and connecting the flushing channel with the frontal passageway,
   wherein
   the frontal passageway narrows, at least within a longitudinal section thereof, towards a distal end of the catheter tip,
   wherein the ratio of the cross-sectional area of the frontal passageway at its narrowest part to the total cross-sectional area of the connecting channels at the distal end thereof is 0.6 to 1.2.

2. The heart catheter according to claim 1, wherein a first distance between the distal end of the narrowing longitudinal section and the distal end of the catheter tip is no more than 0.5 mm.

3. The heart catheter according to claim 2, wherein a second distance between a proximal end of the narrowing longitudinal section and the distal end of the connecting channels is no more than 1 mm.

4. The heart catheter according to claim 1, wherein the passageway narrows at an angle of 1 to 10° with regard to a central axis of the catheter tip.

5. The heart catheter according to claim 1, wherein the cross-sectional area of the frontal passageway at its narrowest part is by a factor of 1.5 to 3 greater than the total cross-sectional area of the connecting channels at the distal end thereof.

6. The heart catheter according to claim 1, wherein the fiber mount comprises ridges separately extending from the main body to the optical fiber and having free inner ends that do not touch each other.

7. The heart catheter according to claim 6, wherein the ridges comprise concave inner centering surfaces adapted to a cylindrical outer surface of the optical fiber.

8. The heart catheter according to claim 6, wherein the ridges comprise proximal sections extending from the main body in a proximal direction and being configured to radially support the catheter hose.

9. The heart catheter according to claim 8, wherein the proximal sections of the ridges comprise longitudinal notches configured to support electric cables/leads.

10. The heart catheter according to claim 1, further comprising electrodes extending from, or being connected with, electric cables enclosed by the catheter hose, the electrodes being supported by longitudinal notches formed in an outer surface of the main body.

11. The heart catheter according to claim 10, wherein the electrodes are stripped distal sections of the electric cables.

12. The heart catheter according to claim 1, wherein the main body and the fiber mount consist of an additively layered biocompatible plastic material.

13. The heart catheter according to claim 1, wherein the optical fiber is configured to emit the laser light at a full divergence angle of 40-80°.

14. A laser system for endocardial laser irradiation, comprising:
   a heart catheter for endocardial laser irradiation, with a catheter hose enclosing a flushing channel and an optical fiber, and with a distal catheter tip comprising:
      a main body surrounding a frontal passageway for laser light emitted from the optical fiber and for a flushing liquid provided via the flushing channel;
      a fiber mount inwardly extending from the main body, for centrally mounting the optical fiber; and
      connecting channels segmenting the fiber mount in a circumferential direction and connecting the flushing channel with the frontal passageway,
   wherein
      the frontal passageway narrows, at least within a longitudinal section thereof, towards the distal end of the catheter tip, and wherein the ratio of the cross-sectional area of the frontal passageway at its narrowest part to the total cross-sectional area of the connecting channels at the distal end thereof is 0.6 to 1.2;
   a laser configured to be coupled with the heart catheter and to provide IR laser light; and
   a flushing pump configured to be coupled with the heart catheter and to provide the flushing liquid.

* * * * *